United States Patent [19]

Notermans et al.

[11] Patent Number: 5,149,632
[45] Date of Patent: Sep. 22, 1992

[54] METHOD FOR THE DETECTION OF MOLDS IN FOODSTUFFS AND HUMAN AND ANIMAL BODY FLUIDS

[75] Inventors: Servatius H. W. Notermans, Bilthoven; Jacobus H. Van Boom, Voorschoten; Gerrit H. Veeneman, Oegstgeest, all of Netherlands

[73] Assignee: De Staat Der Nedelranden Vertengwoordigd Door De Minister Van Welzijn, Rijswijk, Netherlands

[21] Appl. No.: 296,718

[22] Filed: Jan. 12, 1989

[30] Foreign Application Priority Data

Jan. 13, 1988 [NL] Netherlands ............... 8800073

[51] Int. Cl.$^5$ .................................. G01N 33/569
[52] U.S. Cl. ............................ 435/7.31; 435/7.92; 435/7.93; 435/967; 436/534
[58] Field of Search ............... 435/7, 913, 933, 7.31; 436/518, 527, 533, 534

[56] References Cited

PUBLICATIONS

Bennett et al., "Galactofuranosyl Groups are Immunodominant in *Aspergillus fumigatus* Galactomannan", Mol. Immunol. 22(3) pp. 251-254, 1985.
Veeneman et al., "Solid-Phase Synthesis of a Naturally Occurring (3-(1-5)-Linked D-Galactofuranosyl Heptamer Containing the Artificial Linkage Arm L-Homoserine" Tetrahedron Lett. 28 (52) pp. 6695-6698 1987.
J. F. Preston III et al., Chemical Abstracts, Oct. 26, 1970, vol. 73, No. 17, p. 186.
J. E. Bennett et al., Chemical Abstracts, Jun. 24, 1985, vol. 102, No. 25, p. 458.
G. H. Veeneman et al., Chemical Abstracts, Dec. 7, 1987, vol. 107, No. 23, p. 625.

Notermans et al., International Journal of Food Microbiology, 1985, pp. 247-258, vol. 2.
Suzuki, et al., Carbohydrate Research, 1975, vol. 40, pp. 193-197.
Mota et al., Immunochemistry, 1978, vol. 15, pp. 639-640.
Koper et al., Journal of Food Safety, 1980, vol. 2, pp. 35-45.
Jurgens et al., J. Exp. Med., 1987, vol. 165, pp. 720-732.
Chhatwal et al., Medical Microbiology and Immunology, 1987, vol. 176, pp. 1-12.
Essink et al., Journal of Immunological Methods, 1985, vol. 80, pp. 91-96.
Notermans et al., Journal of Applied Bacteriology, 1987, vol. 62, pp. 157-166.
Veeneman et al., Recueil des Travaux Chimiques des Pays-Bas, 1987, vol. 106, pp. 129-131 (English translation attached).
Augestad et al., Acta Chemica Scandinavica, 1954, vol. 8, pp. 251-256.

*Primary Examiner*—Esther L. Kepplinger
*Assistant Examiner*—Carol E. Bidwell
*Attorney, Agent, or Firm*—Brumbaugh, Graves Donohue & Raymond

[57] ABSTRACT

Erroneous-positive results free method for the detection of moulds in foodstuffs and in human and animal body fluids with the aid of an immunological determination of the extracellular polysaccharide (EPS) produced by the mould; this method is characterized in that (a) an immunological determination of the EPS produced by the mould is carried out and, in the case of a positive result, subsequently (b) an immunological determination is carried out in the presence of a synthetically prepared epitope of the EPS investigated and the EPS investigated itself.

4 Claims, 2 Drawing Sheets

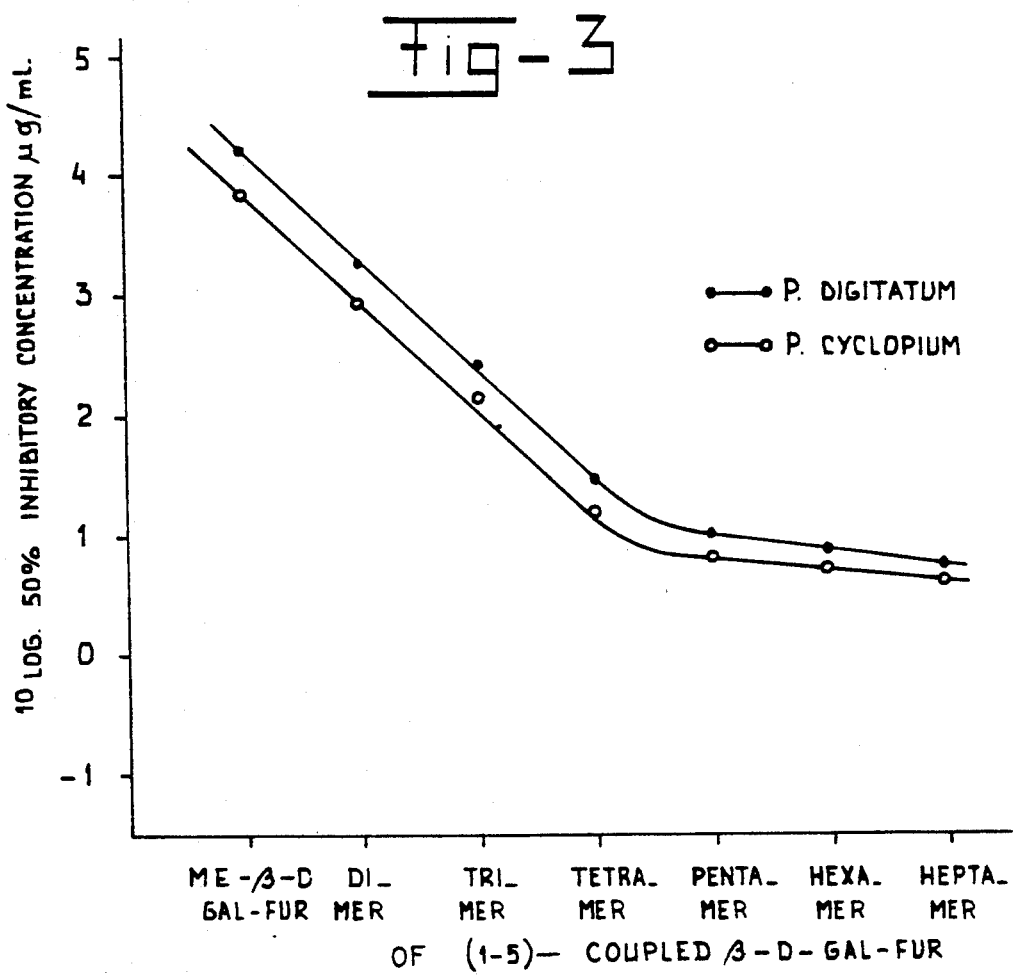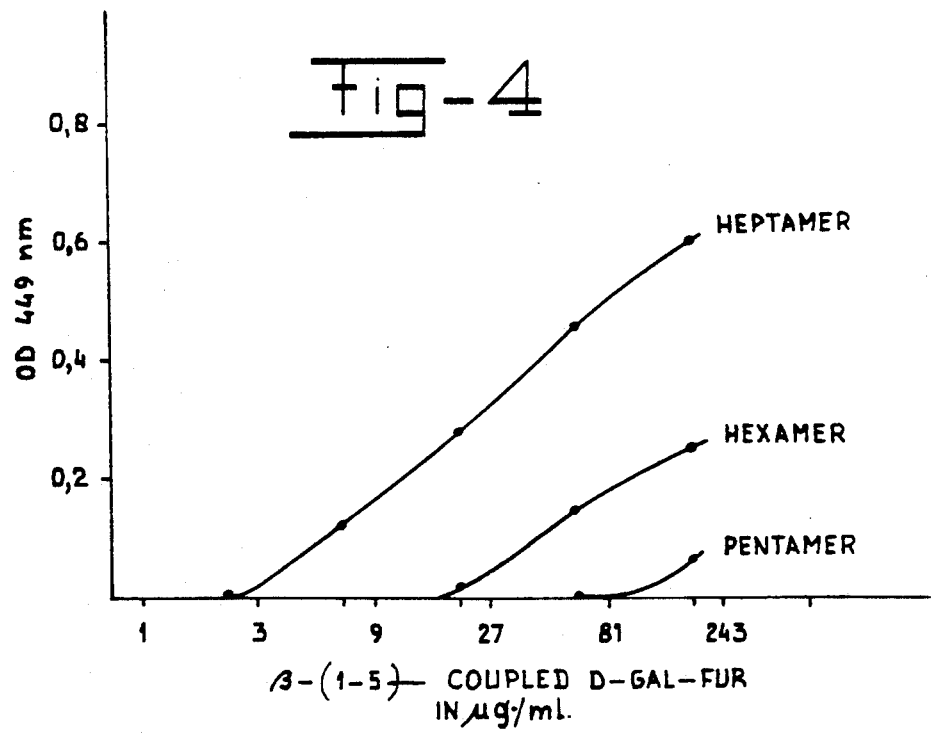

METHOD FOR THE DETECTION OF MOLDS IN FOODSTUFFS AND HUMAN AND ANIMAL BODY FLUIDS

The invention relates to a method for the detection of moulds in foodstuffs and/or raw materials for these and human and animal body fluids with the aid of an immunological determination of the extracellular po (EPS) produced by the mould.

BACKGROUND OF THE INVENTION

Moulds are widely distributing in nature. In addition to their useful characteristics, such as the production of antibiotics and enzymes, they can also cause harm to humans and animals; indirectly by rendering food unfit for consumption and directly by means of infections. The loss of food as a consequence of it becoming mouldy is estimated at 1% of the annual production. In addition to the economic loss as a consequence of rotting, a public health problem also arises as a result of food growing mouldy, specifically as a consequence of the production of mycotoxins. Even when food or the raw materials for this are slightly contaminated with mould, they can already contain mycotoxins. Because of their stability, mycotoxins of this type are not or are hardly inactivated during the production process of the foodstuff, so that it is possible for the mycotoxins to end up in the foodstuffs to be consumed. It is generally known that testing for the presence of mycotoxins in foodstuffs is a time-consuming process, if only because of the large number of mycotoxins which is known at present. For example, moulds belonging to the genus Alternaria produce ten different mycotoxins. Testing for the presence of mycotoxins is then also usually restricted to the detection of aflatoxin, a carcinogen which is produced, inter alia, by species of the genus Aspergillus. In view of the frequency with which moulds produce mycotoxins a check of foodstuffs should also be based on the presence of moulds.

Over the years a number of methods have been developed for the determination of moulds in foodstuffs. These methods can be subdivided into;
a) the culture method;
b) the detection of heat-stable enzymes;
c) the microscopic method; and
d) the chemical methods.

The abovementioned methods all have a number of disadvantages, which are explained in more detail below.

Re a). When the "culture method" is used, samples are transferred to a suitable medium in which the mould can multiply. The degree to which it multiplies is a measure for the initial mould formation. The disadvantage of this method is, however, that only viable moulds can be detected. Therefore, it is usually not possible to determine with this method whether a foodstuff has been prepared from mouldy raw materials.

Re b). The method involving the "detection of heat-stable mould enzymes" runs into technical problems when testing foodstuffs, in view of the fact that such enzymes can also occur naturally in the foodstuff to be tested.

Re c). With the "microscopic method" foodstuffs are examined microscopically for the presence of mould mycelium. Usually the so called Howard Mould Count is used for this purpose. A disadvantage of this widely used method is its laborious nature and the wide variation in results.

Re d). With the "chemical methods" substances specific for moulds are determined, such as chitin or ergosterol. For the determination of chitin, a cell wall constituent of the mould, chitin is converted to glucosamine, which subsequently is determined, for example colorometrically. However, this method is complex. Moreover, glucosamines also arise in non-mouldy foodstuffs. Similar objections also apply in the case of ergosterol determination.

To summarize, it can be stated that all of the methods currently in use for the determination of moulds in foodstuffs and the like have significant shortcomings.

BRIEF DESCRIPTION OF THE INVENTION

Studies by the applicant have shown that moulds produce an extra-cellular polysaccharide (EPS) with powerful antigenic properties. The antigen concerned is virtually genus-specific, i.e. moulds which belong to the same genus or to a closely related genus produce an immunologically identical EPS. Thus, all Penicillium varieties and all Aspergillus varieties produce an immunologically identical EPS. These two genera are those most frequently isolated (approximately 90%) from mouldy foodstuffs.

BRIEF DESCRIPTION OF THE DRAWINGS

FIG. 3 show concentrations of methyl-$\beta$-D-glactofuranoside and various radicals of $\beta$-(1-5)-coupled D-galactofurnose for inhibition of rabbit anti-EPS antibodies.

FIG. 4 shows binding of pentamer, hexamer and heptamer radicals of $\beta$-(1-5)-coupled D-galactofuranose to anti-EPS antibodies.

DETAILED DESCRIPTION OF THE INVENTION

Figure 1:
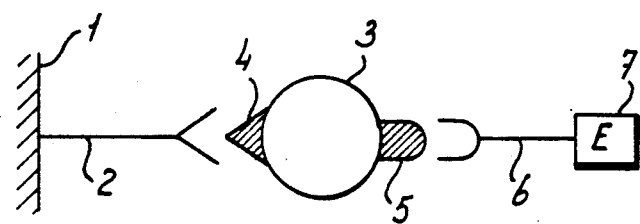
FIG. 1 is a schematic representation of the sandwich ELISA for EPS.

The EPS antigen referred to above, which has the presumed general formula given below

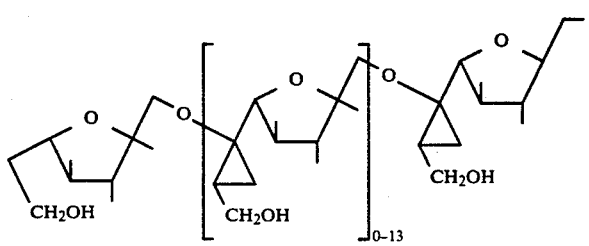

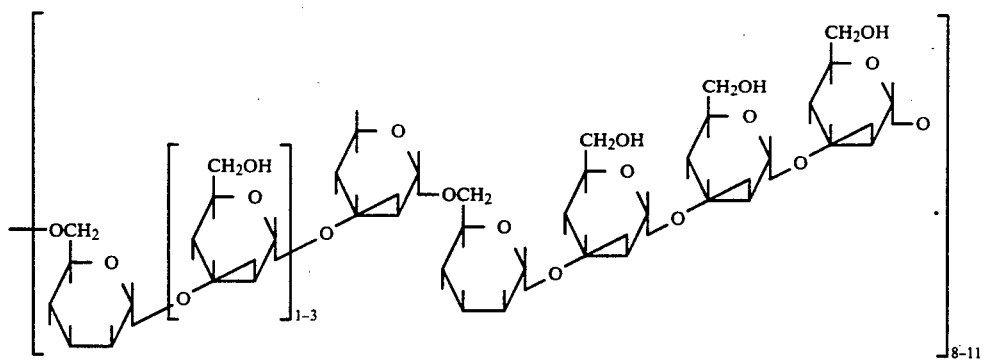

can, for example, be produced by allowing a Penicillium or Aspergillus mould to grow for 7 to 10 days on dialysed malt extract (S. Notermans et al. (1985), Int. J. Food Microbiol. 2, 247-258). The purification of the EPS is effected by means of an ammonium sulphate treatment of the culture fluid followed by a gel filtration. The β-D-galactofuranose which occurs in the EPS from the Penicillium and Aspergillus varieties (see left portion of above formula) appears to be immunodominant.

In connection with the above it is pointed out for the sake of completeness that polysaccharides which are extracted from the cell wall of moulds (CPS) likewise possess immunological properties but, in contrast to the extracellular polysaccharide (EPS) purified from the culture fluid, are not genus-specific. (Suzuki en Takeda, (1975), Carbohydrate Research, 40, 193-195).

With the EPS antigen of moulds it is possible, for example, to evoke antibodies in rabbits. A sandwich ELISA (Enzyme-Linked Immunosorbent Assay) can be developed with these antibodies. With the aid of an ELISA of this type it would then be possible to determine the particular mould genus in a simple manner. After all, mould mass and the EPS antigen produced by the mould are correlated with one another under virtually all growth conditions. The EPS antigen, which is heat-stable, can be extracted by means of a simple treatment (boiling with a phosphate-buffered physiological saline solution) from the foodstuff or raw material to be tested.

However, it has been found that immuno-assays such as the ELISA method can lead to erroneous positive reactions when substances are present in the test samples which can bind to the antibodies in some way. Substances which can lead to erroneous positive reactions of this type are, for example, protein A, which is produced by staphylococci (Mota et al., (1978) Immunochem. 15, pages 639-642). This substance is able to link IgG to one another by binding to the Fc portion of the IgG (Koper et al., (1979), J. Food Safety 2, pages 35-45). Another substance is protein B, which is produced by certain streptococci (Jürgens et al., (1987), J. Exp. Med. 165, pages 720-732) and the IgG-binding proteins, which have not yet been characterized in more detail (Chatwall et al., (1987), Med. Microbiol. Immun. 176, pages 1-12), being able to bind immunoglobulin and, thus, to cause erroneous positive results. Other examples of substances which are capable of producing erroneous positive reactions in immuno-assays such as the ELISA method are, inter alia, lysozyme (Essink et al., (1985), J. Immunol. Meth., 80, 91-96) and extracts of, inter alia, walnuts.

As is evident from the above, the reliability of the results obtained with the aid of immuno-assays such as ELISA is inadequate. The object of the invention is, now, to develop a detection method for the identification of erroneous positive reactions in the immunological determination of moulds, in particular Penicillium and Aspergillus species so that it is possible to speak of a mould infection with certainty.

It has been found that the object defined above can be achieved when a) an immunological determination of the extracellular polysaccharide (EPS) produced by the mould is carried out and, in the case of a positive result, subsequently b) an immunological determination is carried out in the presence of a synthetically prepared epitope of the EPS investigated and the EPS investigated itself.

Figure 2:
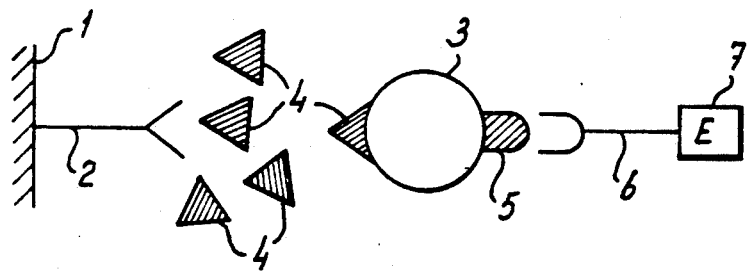
FIG. 2 is a schematic representation of the inhibition ELISA test where a synthetic epitope of EPS effectively inhibits binding of EPS to the antibody.

More particularly, the principle of the "specific inhibition" method according to the invention can be illustrated with the aid of FIG. 1 and FIG. 2.

In FIG. 1 the principle of an ELISA is shown. An antibody IgG (2) is coupled to a support (1). The antigen (3) binds via the Δ-epitope (4) to the IgG. Subsequently an antibody IgG (6), to which an enzyme (7) is bound, is coupled to the epitope (5) of the bound antigen (3). With this method the enzyme activity, such as a colour reaction, is a measure for the amount of antigen present.

In FIG. 2 the principle of the "specific inhibition" method according to the invention is shown. As already defined above, a quantity of synthesized epitope (4) is added to the sample with an antigen (3). These epitopes (4) are intended to prevent the antigen (3). binding to the antibody (2), which is coupled to support (1). The antigen (3) will therefore be removed on rinsing. When an antibody (6) with an enzyme (7) is then added to the system no combination will occur and this will therefore result in a negative ELISA test. The molar ratio of the epitope (4) to the antigen (3) is at least 1;1, advantageously 2;1 to 50:1 and preferably 2:1 to 10;1.

The method according to the invention can advantageously be used for the detection of moulds of the genera Aspergillus and Penicillium. More particularly, this embodiment is characterized in that a) an immunological determination of the EPS of moulds of the genera Aspergillus and/or Penicillium is carried out and, in the case of a positive result, subsequently b) an immunological determination is carried out in the presence of a trimer and/or tetramer of (1-5) coupled β-D-galactofuranose as synthetically prepared epitope of the EPS investigated and the EPS investigated.

A tetramer of (1-5) coupled β-D-galactofuranose is preferably used as the synthetically prepared epitope in step (b) of the latter embodiment.

The ELISA method and the latex agglutination method are mentioned as examples of immuno-assays which can be employed with the invention.

In addition to moulds of the genera Aspergillus and Penicillium, species belonging to the genera Geotrichum, Fusarium, Cladoporium, Mucor and Rhizopus likewise produce genus-specific EPS antigens, the antigens produced by Mucor and Rhizopus being immunologically related. More particularly it is pointed out in this connection that in the EPS of the genus Mucor the D-fucose is immunodominant, so that on the basis of this a "specific inhibition" method can also be developed for this genus, which method also falls within the scope of the invention.

The invention can be applied in many fields, in particular in testing foodstuffs and raw materials used for these. In this connection it is emphasized that research has shown that the EPS which is separated by moulds does not occur in non-mouldy products such as grain, milk, meat, vegetables and fruit and the like. A detection of moulds with the aid of an ELISA which determines the mould EPS can then also be carried out on all foodstuffs and animal feeds (with the exception of the products fermented by moulds; in the case of fermented products it is possible to check whether the fermentation has proceeded as desired). In consideration of the heat stability of the EPS it is even possible to check to what extent the raw materials which were used for the preparation of foodstuffs were mouldy.

A further application of the method according to the invention is the use thereof as pre-screening of samples which are tested for mycotoxins. Only those samples which contain mould EPS have to be tested for mycotoxins.

The invention is illustrated in more detail with the aid of the tests below using the extracellular polysaccharide (EPS) of species of the genera Pencillium and Aspergillus. However, these tests must not be construed as being restrictive.

A) Preparation of extracellular polysaccharides (EPS)

P. digitatum H236, P. dierckxii M90, P. cyclopium RIV129, P. funiculosum H792-2, A. fumigatus M51-1, A. repens H813-1 and A. niger RIV85 spores were inoculated in a malt extract (Notermans et al., (1987), J. Appl. Bact. 62, pages 157-166). After an incubation for 6 days at 24° C with shaking (100 revolutions/min), the culture fluid was separated off by means of a Buchner funnel using Whatman no. 2 filter paper. The filtrate was then freeze-dried and the polysaccharide was isolated therefrom. For this purpose the freeze-dried culture fluid was dissolved in an 80 per cent saturated $(NH_4)_2SO_4$ solution (2.5 ml/g). After shaking vigorously for 3 hours, the mixture was centrifuged for 30 minutes at 15,000×g at 4° C. and then filtered in the manner described above in order to remove the insoluble materials. The filtered fluid was introduced into a Sepharose CL-4B column (2.5×105 cm) which was equilibrated with distilled water. The elution was likewise carried out with distilled water. The immunologically active EPS peak was freeze-dried.

B) Antibody preparation

Antibodies against extracellular polysaccharides of P. digitatum and P. cyclopium were prepared by immunizing rabbits in the following way: portions of 0.25 mg, 0.25 mg and 0.5 mg EPS were injected subcutaneously on days 1, 4 and 30. In the first two injections the portions were mixed with Freund's complete adjuvant. For the last injection the portion was mixed with Freund's incomplete adjuvant. The IgG fraction was isolated by the method of Steinbuch and Audran (1969) and freeze-dried.

TABLE A

| Increase in antibody titer* in rabbits which were immunized with purified EPS from P. digitatum | |
|---|---|
| Day | Titer |
| −1 | <50 |
| 3 | <50 |
| 29 | 6,000 |
| 38 | 50,000 |

*A titer is the reciprocal value of the dilution of the serum which just still gives a positive result in the ELISA.

C) Human sera

A total of 40 serum samples were collected arbitrarily from healthy Dutch males and females aged between 15 and 65.

D) Chemical synthesis of various β-linked galactofuranosylsaccharides

Methyl β-D-galactofuranoside was obtained by chromatography of a mixture of methyl-D-galactosides over Whatman cc 31 microgranular cellulose (Augestad and Berner (1954), Act. Chem. Scand. 8, pages 251–256).

The β-(1-5)-coupled galactofuranosyl dimer, trimer and tetramer (Veeneman et al., 1987, Recl. Trav. Chim. Pays-Bas 106. pages 129-131) and the β-(1-2)-, β-(1-3)- and β-(1-6)-dimers were synthesized by coupling monomer residues substituted in the correct manner via the Helferich procedure. In addition the pentamer, hexamer and heptamer of the β-(1-5)-coupled galactofuranoside were synthesized (Veeneman et al., (1988), Ned. Trav. Chim. Pays-Bas, in press).

E) Inhibition characteristics

The inhibition characteristics were determined using a "competition" enzyme-linked immunosorbent assay (ELISA). Microtiter polyvinyl wells (Cooke, Dynatech) were coated with polysaccharides which had been isolated from culture fluids of moulds. For this purpose 0.1 ml of 0.07 M phosphate buffer, pH 7.2, with 0.15 M NaCl (PBS) and 1 μg polysaccharide were added to each well of the plate. After incubating for one night with shaking at 20° C., the wells were washed under a continuous stream of tap water with 0.05% Tween 20 for 0.5 min. A prepared mixture of 50 μl antibodies (rabbit IgG and human sera respectively), diluted in PBS, which contained 0.05% Tween 20 and 2% bovine serum albumin, and 50 μl inhibitor, which was diluted in the same buffer, were then added. After an incubation time of 60 minutes the wells were washed in the manner described above. The quantity of antibodies which was absorbed on the polysaccharides was determined with sheep-anti-rabbit-globulins and with sheep-anti-human-globulins respectively which were conjugated to peroxidase. For this purpose 0.1 ml conjugate diluted in PBS, which contained 0.05% Tween 20, was added to each well (dilution was checked using the checker board titration). The incubation and the washing were carried out in the manner described for the prepared test sample (mixture of serum or IgG and inhibitor).

The enzyme reaction was determined spectrophotometrically at 449 nm after adding a solution of 5-aminosalicylic acid and $H_2O_2$ (0.1 ml 0.07% 5-amino-salicylic acid, pH 6.0, and 0.005% $H_2O_2$ were added to each well) and an incubation for 30 minutes at 20° C.

The human serum and rabbit IgG solutions were diluted to concentrations at which the extinction coefficients without inhibitor start to decrease (extinction value approximately 0.70). Methyl-$\beta$-D-galactofuranoside and the dimers to heptamers inclusive of (1-5)-coupled $\beta$-D-galactofuranosides were used as inhibitors. The inhibition effect of dimers of (1-2)-, (1-3)- and (1-6)-coupled $\beta$-D-galactofuranoside was also investigated (see Table B). The percentage inhibition was calculated as 100—100 (extinction with inhibitor - extinction without inhibitor).

F) Antibody binding experiments

A sandwich ELISA was used to ascertain whether (1-5)-coupled $\beta$-D-galactofuranosyl radicals were capable of binding antibodies. 0.1 ml portions containing 10 μg/ml rabbit IgG anti-EPS, which was diluted in PBS, were introduced into wells of polyvinyl plates and incubated overnight with shaking at 20° C. After washing in the manner described above, 0.1 ml samples containing $\beta$-(1-5)coupled galactofuranosyl radicals in PBS with 0.05% Tween 20 and 2% bovine serum albumin were added. After an incubation time of 60 minutes the plates were washed. 0.1 ml of an optimum dilution (=dilution was checked using the checker board titration) of rabbit IgG anti-EPS, conjugated with peroxidase, diluted in PBS with 0.05% Tween 20 was then added to each well. The incubation and the washing were carried out in the manner described above. The enzyme reaction was also determined in the manner described above.

G) Results

The inhibition, described under (E), of the binding of antibodies evoked in rabbits to EPS with the aid of methyl-$\beta$-D-galactofuranoside and $\beta$-(1-5)-coupled D-galactofuranosyl radicals is shown in FIG. 3. Methyl-$\beta$-D-galactofuranoside and dimers, trimers and tetramers of (1-5)-coupled $\beta$-D-galactofuranosides interfere to an increasing degree in the reaction between the polysaccharide antigen and the antibody evoked in rabbits. The pentamer, hexamer and heptamer also display an increasing interference, but to a much lesser degree. The chemical synthesis used produced no differences in the activity of the inhibitors. The 50 per cent inhibition concentration of the monomer was approximately 10,000 μg/ml. For the dimer, trimer, tetramer, pentamer, hexamer and heptamer, these concentrations were 1000, 250, 30, 10, 6 and 4 μg/ml. The quantity of EPS of P. digitatum itself which causes a 50 per cent inhibition of the binding of rabbit IgG to the EPS of P. digitatum was 2 μg/ml. For the EPS of P. cyclopium this quantity was 0.4 μg/ml. A complete inhibition (100%) was observed with the trimer, tetramer, pentamer, hexamer and heptamer of (1-5)-coupled $\beta$-D-galactofuranosides at concentrations of 1000, 100, 30, 20 and 15 μg/ml.

For the sake of comparison the inhibition effects of the dimers of (1-2)-, (1-3)-, (1-5)- and (1-6)-coupled $\beta$-D-galactofuranosides are also given in Table B below.

TABLE B

Inhibition of antibody binding to extracellular polysaccharides (EPS) of P. digitatum and P. cyclopium by dimers of $\beta$-coupled D-galactofuranosides

| | 50% inhibition concentration (μg/ml) | |
|---|---|---|
| | EPS of P. digitatum | EPS of P. cyclopium |
| (1-5) coupled | 3,000 | 1,000 |
| (1-3) coupled | 16,000 | 6,000 |
| (1-2) coupled | 32,000 | 11,000 |
| (1-6) coupled | 40,000 | 16,000 |

As can be deduced from Table B above, of the various dimers the (1-5)-coupled $\beta$-D-galactofuranoside was found to give the greatest inhibition effect in the binding of rabbit antibody to polysaccharides of P. digitatum and P. cyclopium. The inhibition effect of the other dimers was much less and more related to that of the monomer (see also FIG. 3).

With a view to the possibility of erroneous positive ELISA reactions occurring, the (1-5-coupled $\beta$-D-galactofuranosyl compounds were (after entering into binding with the (firmly attached) antibody against the EPS of P. digitatum or P. cyclopium) also tested using the test described under (F) to determine their capacity for again binding antibodies against the EPS of P. digitatum and P. cyclopium. Of the compounds concerned, the pentamer, hexamer and heptamer were able to bind these antibodies to an increasing degree (see FIG. 4), which therefore results in erroneous positive ELISA reactions. On the basis of this, only the relevant trimer and tetramer can be used for the "specific inhibition" according to the invention. At the same time no differences were observed in binding capacities between the antibodies against the EPS of P. digitatum and of P. cyclopium.

The inhibition of the human antibody binding to EPS of moulds was tested with 40 serum samples using the tetramer of (1-5)-coupled $\beta$-D-galactofuranoside as inhibitor. The EPS in these tests originated from P. digitatum, P. cyclopium, P. dierckxii, P. funiculosum, A. niger, A. fumigatus and A. repens. Antibodies against P. funiculosum were not detectable in any serum sample, while antibodies against the other EPS derivatives were present in all 40 serum samples. The titers (reciprocal value of the dilution which gives the extinction equal to the mean value for 10 blank samples+2.81×standard deviation of these blank samples; confidence limit 99%), were in a range from 400 to 6,000. There was a significant correlation 99%) between the presence of antibodies in each serum and against the various Penicillium/Aspergillus EPS derivatives which were tested (Spearman Rank correlation test). When, for example, the serum had a high titer for P. digitatum there was a high titer for all other Penicillium and Aspergillus species except for P. funiculosum. The degree of inhibition of the human antibody binding by the tetramer was found to be identical for the various EPS derivatives tested. The results of the inhibition tests were therefore averaged and are summarized in Table C.

TABLE C

Inhibition of human antibody binding of 40 serum samples to extracellular polysaccharides of Penicillium and Aspergillus species by a tetramer of (1–5)-coupled β-D-galactofuranoside

| Concentration of inhibitor used (μg/ml) | Number of samples with an inhibition of | | |
|---|---|---|---|
| | 25% | 50% | 90% |
| 500 | 37 | 36 | 15 |
| 100 | 36 | 32 | 0 |
| 20 | 34 | 12 | 0 |
| 4 | 15 | 0 | 0 |

In addition an immunological determination, described under (F), of Penicillium and Aspergillus species was carried out on 16 samples of walnuts and 9 samples of herbs, use being made of rabbit IgG and, respectively 50 μg/ml of a framer of (1–5)-coupled β-D-galactofuranoside per test sample. The EPS antigen possibly present in the abovementioned products was extracted by boiling with a phosphate-buffered physiological saline solution. The test results are summarized in Table D.

TABLE D

| Number of samples | ELISA titer* | Number of samples with inhibition >50%** |
|---|---|---|
| Nuts | | |
| 3 | 100–500 | 3 |
| 9 | 500–5000 | 7*** |
| 4 | 5000–50,000 | 4 |
| Herbs | | |
| 5 | 5000–50,000 | 5 |
| 4 | >50,000 | 4 |

*Titer is the reciprocal value of the dilution which gives the extinction equal to the mean value for 10 blank samples + 2.81 × standard deviation of these blank samples; confidence limit 99%.
**Inhibition test was carried out with samples which were diluted such that an ELISA extinction of approximately 0.70 was obtained.
***Two samples (both walnuts) were found to give an extinction which could not be neutralized by addition of the tetramer. There is thus an erroneous positive reaction here.

We claim:

1. A method for the detection of a mold in a sample comprising the steps of:
   (a) combining a portion of the sample with an antibody that specifically binds to an extracellular polysaccharide produced by the mold and determining the binding of a component in the sample with the antibody;
   (b) if binding is detected in step (a), combining another portion of the sample, the antibody and an amount of a synthetically prepared epitope of said extracellular polysaccharide sufficient to effectively block all binding of said antibody to the extracellular polysaccharide present in the sample and determining the presence or absence of the binding of a component in the sample with the antibody wherein the presence of binding indicates a false positive result and the absence of binding indicates the presence of mold in the sample.

2. A method for detecting the presence of molds of the genera Aspergillus and Penicillium and in a sample comprising the steps of:
   (a) combining a portion of the sample with an antibody that specifically binds to an extracellular polysaccharide produced by the molds of the genera Aspergillus and Penicillium and determining the binding of a component in the sample with the antibody;
   (b) if binding is detected in step (a), combining another portion of the sample, the antibody and an amount of a synthetically prepared timer or tetramer of (1–5)-coupled β-D-galactofuranose sufficient to effectively block all binding of said antibody to the extracellular polysaccharide present in the sample and determining the presence or absence of the binding of a component in the sample with the antibody wherein the presence of binding indicates a false positive result and the absence of binding indicates the presence of mold in the sample.

3. The method according to claim 2, wherein the extracellular polysaccharide is a tetramer of (1–5)-coupled β-D-galactofuranose.

4. The method according to claim 1, 2 or 3 wherein the immunological determination comprises an ELISA reaction or a latex agglutination reaction.

* * * * *

UNITED STATES PATENT AND TRADEMARK OFFICE
CERTIFICATE OF CORRECTION

PATENT NO. : 5,149,632
DATED : September 22, 1992
INVENTOR(S) : Servatius H. W. Notermans It is certified that error appears in the above-indentified patent and that said Letters Patent is hereby corrected as shown below:

Col 2., lines 17-18, delete "(English translation attached)".
Col. 1, line 9, "po" should read --polysaccharide--;
    line 13, "distributing" should read --distributed--;
Col. 2, line 26, "DESCRIPTION" should read --SUMMARY--;
    line 45, "show" should read --shows--.
    line 45, "glac-" should read --galac- --;
Col. 5, line 3, "8-D-" should read --ß-D- --;
    line 14, "Cladoporium" should read --Cladosporium--;
Col. 7, line 15, "galactofuranoside" should read --galactofuranosides--;
Col. 8, line 57, "99%)" should read --(>99%)--;
Col. 9, line 17, "framer" should read --tetramer--;
Col. 10, line 17, "and in" should read --in--;
    line 27, "timer" should read --trimer--.

Signed and Sealed this

Fourteenth Day of December, 1993

Attest:

BRUCE LEHMAN

*Attesting Officer*     *Commissioner of Patents and Trademarks*